US00PP21610P2

(12) United States Plant Patent
Danziger

(10) Patent No.: US PP21,610 P2
(45) Date of Patent: Jan. 4, 2011

(54) ***IMPATIENS* PLANT NAMED 'DANCEL846'**

(50) Latin Name: *Impatiens Hawkeri*
Varietal Denomination: DANCEL846

(75) Inventor: Gavriel Danziger, Moshav Nir-Zvi (IL)

(73) Assignee: Danziger "Dan" Flower Farm, Moshav Mishmar Hashiva (IL)

( * ) Notice: Subject to any disclaimer, the term of this patent is extended or adjusted under 35 U.S.C. 154(b) by 0 days.

(21) Appl. No.: 12/583,697

(22) Filed: Aug. 25, 2009

(51) Int. Cl.
*A01H 5/00* (2006.01)

(52) U.S. Cl. ..... Plt./318.1

(58) Field of Classification Search ..... Plt./318.1
See application file for complete search history.

(56) References Cited

PUBLICATIONS

UPOV ROM GTITM Computer Database, GTI Jouve Retrieval Software 2010/03 Ciation for 'DANCEL846'.*

* cited by examiner

*Primary Examiner*—Wendy C. Haas
(74) *Attorney, Agent, or Firm*—Audrey Charles

(57) ABSTRACT

A new and distinct cultivar of *Impatiens* plant named 'DANCEL846', characterized by its dark pink and red-orange bicolored flowers, dark green-colored foliage, and moderately vigorous, compact-mounded growth habit, is disclosed.

1 Drawing Sheet

Latin name of genus and species of plant claimed: *Impatiens Hawkeri.*

Variety denomination: 'DANCEL846'.

BACKGROUND OF THE INVENTION

The present invention relates to a new and distinct cultivar of *Impatiens* plant botanically known as *Impatiens Hawkeri* and hereinafter referred to by the cultivar name 'DANCEL846'.

The new cultivar originated in a controlled breeding program in Moshav Mishmar Hashiva, Israel during December 2004. The objective of the breeding program was the development of *Impatiens* cultivars with numerous large flowers, excellent basal branching, and a compact-mounded growth habit.

The new *Impatiens* cultivar is the result of cross-pollination. The female (seed) parent of the new cultivar is the proprietary *Impatiens Hawkeri* breeding selection designated NG-4-3747, not patented, characterized by its dark pink and red bicolored flowers, dark green-colored foliage, and moderately vigorous, compact-mounded growth habit. The male (pollen) parent of the new cultivar is the proprietary *Impatiens Hawkeri* breeding selection designated NG-4-3758, not patented, characterized by its pink and orange bicolored flowers, medium green-colored foliage, and moderately vigorous, compact-mounded growth habit. The new cultivar was discovered and selected as a single flowering plant within the progeny of the above stated cross-pollination during July 2005 in a controlled environment at Moshav Mishmar Hashiva, Israel.

Asexual reproduction of the new cultivar by terminal stem cuttings since July 2005 at Moshav Mishmar Hashiva, Israel and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'DANCEL846' as a new and distinct cultivar of *Impatiens* plant:

1. Dark pink and red-orange bicolored flowers;
2. Dark green-colored foliage; and
3. Moderately vigorous, compact-mounded growth habit.

Plants of the new cultivar differ from plants of the female parent primarily in flower color and from plants of the male parent primarily in flower color and foliage color.

Of the many commercially available *Impatiens* cultivars, the most similar in comparison to the new cultivar is HARMONY Pink Cream 'Danharpkcream', not patented. However, in side by side comparisons, plants of the new cultivar differ from plants of 'Danharpkcream' in at least the following characteristics:

1. Plants of the new cultivar have a flower color different from plants of 'Danharpkcream'; and
2. Plants of the new cultivar have fewer flowers than plants of 'Danharpkcream'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'DANCEL846'. The plants were grown in 4.5 inch pots for 10 weeks in a greenhouse at West Chicago, Ill.

DETAILED BOTANICAL DESCRIPTION

Figure 1:
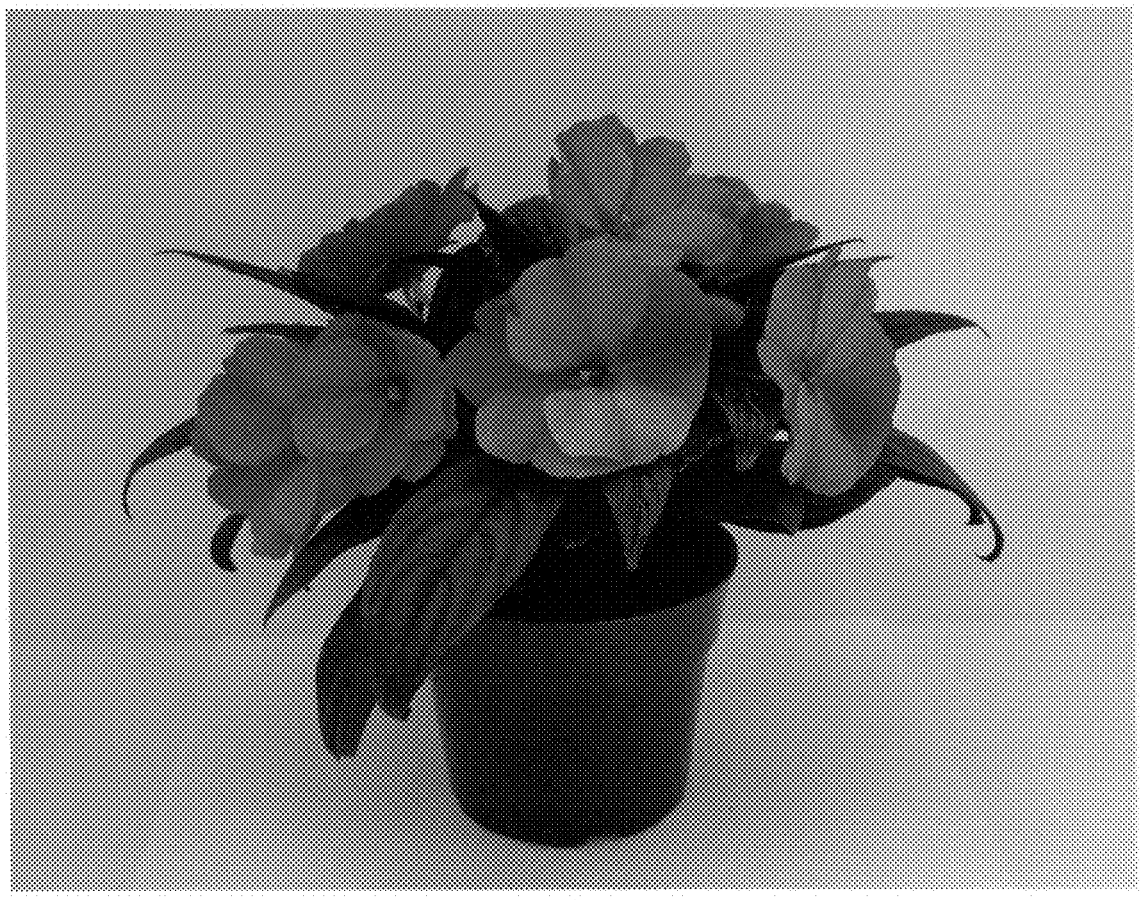
FIG. 1 illustrates a side view of the overall growth and flowering habit of 'DANCEL846'.
Figure 2:
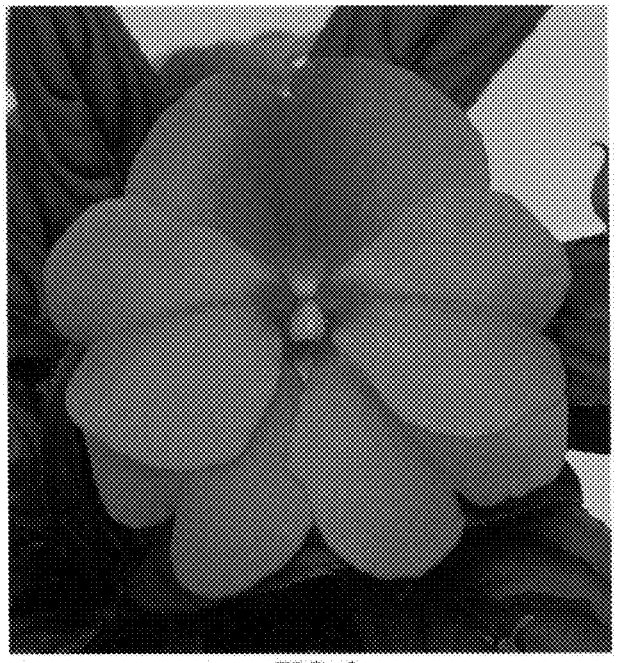
FIG. 2 illustrates a close-up view of an individual flower of 'DANCEL846'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in June 2009 under natural light conditions in West Chicago, Ill.

The following descriptions and measurements describe plants produced from cuttings from stock plants and grown in a glass-covered greenhouse under conditions comparable to those used in commercial practice. The plants were grown at West Chicago, Ill. in 4.5 inch pots for 10 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Impatiens Hawkeri* cultivar DANCEL846.

Parentage:

*Female parent.*—Proprietary *Impatiens Hawkeri* breeding selection designated NG-4-3747, not patented.

*Male parent.*—Proprietary *Impatiens Hawkeri* breeding selection designated NG-4-3758, not patented.

Propagation:

*Type cutting.*—Terminal stem.

*Time to initiate roots.*—Approximately 7 to 8 days.

*Time to produce a rooted cutting.*—Approximately 21 to 24 days.

*Root description.*—Fibrous.

*Rooting habit.*—Freely branching.

Plant description:

*Commercial crop time.*—Approximately 6 to 8 weeks from a rooted cutting to finish in a 10 cm pot.

*Growth habit and general appearance.*—Moderately vigorous, compact, and mounded growth habit.

*Size.*—Height from soil level to top of plant plane: Approximately 14.5 cm. Width: Approximately 25.3 cm.

*Branching habit.*—Freely basal branching. Quantity of main branches per plant: Approximately 4.

*Branch.*—Strength: Strong. Length: Approximately 9.6 cm. Diameter at central internode: Approximately 5.0 mm. Length of central internode: Approximately 2.2 cm. Texture: Glabrous. Color of young stem: 144A with an overlay of 185A. Color of mature stem: 144A with a strong overlay of 185A.

Foliage description:

*General description.*—Quantity of leaves per main branch: Approximately 8. Fragrance: None. Form: Simple. Arrangement: In whorls of 3 to 5 leaves.

*Leaves.*—Aspect: Petiole is at an acute angle to stem and leaf blade is perpendicular to stem. Shape: Elliptic. Margin: Serrate, ciliate. Apex: Acuminate. Base: Attenuate. Venation pattern: Pinnate. Length of mature leaf at center of stem: Approximately 10.7 cm. Width of mature leaf at center of stem: Approximately 3.5 cm. Texture of upper surface: Glabrous. Texture of lower surface: Sparsely pubescent on venation. Color of upper surface of young and mature foliage: Closest to 139A with venation of 187B. Color of lower surface of young and mature foliage: 187B with venation of 187B.

*Petiole.*—Length: Approximately 3.1 cm. Diameter: Approximately 3.0 mm. Texture: Glabrous. Color: 187B.

Flowering description:

*Flowering habit.*—'DANCEL846' is freely flowering under outdoor growing conditions with substantially continuous blooming from spring through autumn and year-round in greenhouse environment.

*Lastingness of individual flower on the plant.*—Approximately 5 to 7 days.

Flower description:

*General description.*—Type: Single. Quantity per plant: Approximately 9. Fragrance: None.

*Bud.*—Rate of opening: Generally takes 3 to 4 days for bud to progress from first color to fully open flower. Quantity showing color per plant: Approximately 3.

*Bud just before opening.*—Shape: Ovoid. Length: Approximately 2.1 cm. Diameter: Approximately 1.4 cm. Color: 45A.

*Corolla.*—Shape: Round, cupped when first open with petals turning downward with age. Width: Approximately 7.3 cm. Depth: Approximately 1.9 cm. Borne: Above and below foliage.

*Petals.*—Quantity: 5. Shape: Obovate. Aspect: Flat. Appearance: Iridescent. Margin: Entire. Apex: Emarginate. Base of upper petal: Truncate. Base of lateral and lower petals: Attenuate. Length of upper petal: Approximately 3.4 cm. Width of upper petal: Approximately 5.4 cm. Length of lateral petals: Approximately 3.5 cm. Width of lateral petals: Approximately 3.6 cm. Length of lower petals: Approximately 3.7 cm. Width of lower petals: Approximately 4.1 cm. Texture of upper and lower surfaces: Glabrous. Color of upper surface when first open: 67B with base and center of 45A on upper petal and a central stripe of 45A on lateral and lower petals. Color of lower surface when first open: 45D. Color of upper surface when fully open: 67C with base and center of 45A on upper petal and a central stripe of 45A on lateral and lower petals. Color of lower surface when fully open: Lighter than 45D.

*Spur.*—Quantity: 1 per flower. Length: Approximately 5.1 cm. Diameter at proximal end: Approximately 2.0 mm. Diameter at distal end: Approximately 1.0 mm. Texture: Glabrous. Color: 145D with tip of 144A.

*Peduncle.*—Strength: Strong. Aspect: Acute angle to stem. Length: Approximately 5.2 cm. Diameter: Approximately 2.0 mm. Texture: Glabrous. Color: 145B often with a faint overlay of 185A nearest flower attachment.

*Sepals.*—Quantity per flower: 4 with one fused to base of upper petal. Shape of lateral sepals: Ovate. Shape of lower sepal: Ovate. Apex of all sepals: Acuminate. Length of lateral sepals: Approximately 1.6 cm. Width of lateral sepals: Approximately 9.0 mm. Length of lower sepal: Approximately 1.9 cm. Width of lower sepal: Approximately 1.4 cm. Texture of upper and lower surfaces of all sepals: Glabrous. Color of upper and lower surfaces of lateral sepals: 185A. Color of upper and lower surfaces of lower sepal: Closest to 45D.

*Reproductive organs.*—Androecium: Stamen quantity: 5 per flower, fused around pistil at apex. Anther shape: Hooded. Anther length: Approximately 2.0 mm. Anther color: 158D. Filament color: 155D with an overlay of N57B. Pollen amount: Abundant. Pollen color: 155D. Gynoecium: Pistil quantity: 1 per flower. Pistil length: Approximately 5.0 mm. Stigma shape: 5-pointed star. Stigma color: 187C. Style color: 144A transitioning to 187A with age. Ovary texture: Glabrous. Ovary color: 144A transitioning to 187A with age.

Seed and fruit production: Neither seed nor fruit production has been observed.

Disease and pest resistance: Resistance to pathogens and pests common to *Impatiens* has not been observed.

What is claimed is:

1. A new and distinct cultivar of *Impatiens* plant named 'DANCEL846', substantially as herein shown and described.

* * * * *